United States Patent [19]

Kondo et al.

[11] Patent Number: 5,665,779
[45] Date of Patent: Sep. 9, 1997

[54] PHARMACEUTICAL COMPOSITION FOR INHIBITING THE INFECTION WITH AIDS VIRUS

[75] Inventors: Shinichi Kondo, Yokohama; Yoko Ikeda, Tokyo; Masa Hamada, Naito-machi; Tomio Takeuchi, Tokyo; Hiroo Hoshino, Maebashi, all of Japan

[73] Assignee: Zaidan, Hojin, Biseibutsu, Kagaku, Kenkyu, Kai, Tokyo, Japan

[21] Appl. No.: 256,121

[22] PCT Filed: Dec. 25, 1992

[86] PCT No.: PCT/JP92/01703

§ 371 Date: Jun. 24, 1994

§ 102(e) Date: Jun. 24, 1994

[87] PCT Pub. No.: WO93/12776

PCT Pub. Date: Jul. 8, 1993

[30] Foreign Application Priority Data

Dec. 27, 1991 [JP] Japan .................. 3-346341

[51] Int. Cl.$^6$ .................. A61K 31/16

[52] U.S. Cl. .................. 514/626
[58] Field of Search .................. 514/626

[56] References Cited

FOREIGN PATENT DOCUMENTS 62-114947  5/1987  Japan .................. 514/626

*Primary Examiner*—Jerome D. Goldberg
*Attorney, Agent, or Firm*—Lalos & Keegan

[57] ABSTRACT

D-β-Lysylmethanediamine represented by the formula (I)

$$H_2NCH_2CH_2CH_2\overset{(R)}{\underset{NH_2}{C}}HCH_2CONHCH_2NH_2 \quad (I)$$

or a salt or a hydrate thereof has now been found to have an activity of inhibiting the infection with AIDS virus (a virus causative of acquired human immunodeficiency syndrome), mamely HIV. A pharmaceutical composition comprising the above compound or a salt or hydrate thereof as active ingredient is provided and expectable as one of remedial agents for treating AIDS which is now thought to be difficult to cure.

1 Claim, No Drawings

PHARMACEUTICAL COMPOSITION FOR INHIBITING THE INFECTION WITH AIDS VIRUS

This application is a 371 of PCT/JP92/01703 filed Dec. 25, 1992.

TECHNICAL FIELD

This invention relates to a pharmaceutical composition for inhibiting infection with a virus causative of acquired human immunodeficiency syndrome, namely AIDS virus (hereinafter sometime abbreviated as HIV), which composition comprises D-β-lysylmethanediamine, a salt or hydrate thereof as active ingredient. This invention also relates to a method for inhibiting the infection of human T-cells with AIDS virus, which comprises treating human T-cells with D-β-lysylmethanediamine, a salt or hydrate thereof. This invention further includes use of D-β-lysylmethanediamine, a salt or hydrate thereof in the manufacture of antiviral composition for inhibiting the infection with AIDS virus.

BACKGROUND ART

AIDS is a disease which is caused due to human T-cells being infected with AIDS virus. AIDS has brought about problems in human society. Several agents for inactivating HIV are reported. However, any of these HIV-inactivating agents is not necessarily satisfactory as a remedial agent for AIDS. Accordingly, there exists an outstanding demand to develope and provide such a new antiviral agent which is of low toxicity but can show a high activity to inhibit the infection of human T-cells with HIV.

On the other hand, D-β-lysylmethanediamine as obtained earlier by the present inventors is an antibiotic which has weak antibacterial activity against Gram-positive bacteria. D-β-Lysylmethanediamine has the unique structure represented by the following formula (I)

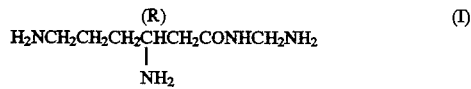

This compound is a known antibiotic which is produced by a microorganism, *Streptomyces nashvillensis* and which was reported by the present inventors (see "Journal of Antibiotics" Vol. 39, No. 3, page 476 (1986) and Japanese patent application first publication "Kokai" Sho-62-114947 specification published 26 May 1987). D-β-Lysylmethanediamine hemi-carbonate (½ $H_2CO_3$) is in the form of a colorless powder which is hygroscopic but has no definite melting point measurable. Its specific optical rotation is $[\alpha]_D^{26}$ −7.4° (c 0.5, water).

An object of this invention is to provide a new antiviral agent which inhibits strongly the infection of human T-cells with HIV but exhibits a low toxicity to mammals and which is expectable to be useful as a remedial agent for AIDS. Another object of this invention is to provide a new pharmaceutical composition which inhibits the infection with AIDS virus. Further object of this invention is to provide a therapeutic method for inhibiting the infection of human T-cells with HIV. Further another objects of this invention will be clear from the following descriptions.

DISCLOSURE OF THE INVENTION

In order to achieve the above-mentioned objects, we, the present inventors, have made extensive investigations. In consequence, the present inventors, have now discovered that D-β-lysylmethanediamine, a salt or hydrate thereof exhibits a high activity for inhibiting the infection of human T-cells with HIV but has a low toxicity to mammals. Thus, according to our experiments, it has been found that when human T-cells which have been treated with D-β-lysylmethanediamine or a salt or hydrate thereof and then incubated in a culture medium are brought into contact with HIV, the infection of the human T-cells with HIV can be inhibited under the action of D-β-lysylmethanediamine or salt or hydrate thereof. Therefore, D-β-lysylmethanediamine, a salt and hydrate thereof have a high activity to inhibit the infection of human T-cells with HIV and, in a broad sense, have an antiviral activity against HIV.

According to a first aspect of this invention, therefore, there is provided a pharmaceutical composition for inhibiting the infection with AIDS virus, namely HIV, which comprises as active ingredient D-β-lysylmethanediamine having the formula (I)

or a salt or a hydrate thereof, in association with a pharmaceutically acceptable carrier for the active ingredient.

In a further aspect, this invention includes a method for inhibiting infection of human T-cells with AIDS virus, which comprises treating human T-cells with D-β-lysylmethanediamine of the formula (I) as shown above, a pharmaceutically acceptable salt or hydrate thereof in an effective amount to inhibit the infection with AIDS virus.

In another aspect, this invention includes use of D-β-lysylmethanediamine of the formula (I), a pharmaceutically acceptable salt or hydrate thereof, in the manufacture of a pharmaceutical composition for inhibiting infection with AIDS virus.

Furthermore, this invention relates also to a process for the manufacture of a pharmaceutical composition for inhibiting infection with AIDS virus, which comprises mixing D-β-lysylmethanediamine, a pharmaceutically acceptable salt or hydrate thereof, with a pharmaceutically acceptable carrier.

BEST EMBODIMENTS FOR WORKING THE INVENTION

D-β-Lysylmethanediamine which is used as active ingredient or active compound according to this invention is a water-soluble substance of the basic nature and hence can form an acid addition salt with an acid, either inorganic or organic. The acids which are available for the formation of said acid addition salt include pharmaceutically acceptable inorganic acids such as hydrochloric acid, sulfuric acid, hydrobromic acid, phosphoric acid, nitric acid and the like, as well as pharmaceutically acceptable organic acids such as acetic acid, malic acid, citric acid, ascorbic acid, methanesulfonic acid and the like.

D-β-Lysylmethanediamine used according to this invention is characterised by its low toxicity to mammalian animals. For instance, in the tests of estimating acute toxicity of this compound where mice were intravenously administered with D-β-lysylmethanediamine, the mice having received administration of D-β-lysylmethanediamine could tolerate a dosage of 250 mg/kg of D-β-lysylmethanediamine without involving their death.

The pharmaceutical compositions according to this invention, which contains D-β-lysylmethanediamine, an acid addition salt or a hydrate thereof as the active ingredient in combination with a pharmaceutically acceptable solid or liquid carrier for the active ingredient, may be formulated into various forms. The so formulated composition according to this invention for inhibiting the AIDS infection may be of conventional preparations such as powders, granules, tablets, syrups, injections and the like for oral administration or parenteral administration.

The following assay tests were conducted in order to demonstrate that D-β-lysylmethanediamine possesses a high activity inhibitory to the infection of human T-cells with HIV, namely the AIDS virus. The procedure for these assay tests is as follows:

Test Example 1

Effects of D-β-lysylmethanediamine inhibitory to infection of human T-cells with HIV were examined in a similar manner to the assay methods described in the "Proc. Natl. Acad, Sci. USA," 80, 6061–6065 (1983); "J. Antibiot.", 40, 1077–1078, (1987); "J. Antibiot.", 42, 344–346 (1989) and "J. Antibiot." 44, 1228–1236 (1991).

$1\times10^5$ Cells/ml of MT-4 cells (human T-cell line) in phosphate buffered saline were seeded into Costar 48-well plates in an amount of 0.5 ml/well. Each well was added with 0.05 ml of a solution of the test compound, namely D-β-lysylmethanediamine (dissolved at different concentrations of 3, 10, 30 and 100 µg per ml in phosphate buffered saline). After incubation for 2 hours at 37° C. under 5% $CO_2$, the MT-4 cells were infected with 0.05 ml of HIV (HTLV-$III_B$ strain) as added in an amount of multiplicity of infection (m.o.i) of 0.025 to 0.05 in each well. The plates were incubated for 4 days at 37° C. under 5% $CO_2$ so that the T-cells were treated in the presence of the test compound at the different concentrations.

Portions of the incubated cultures were taken and the MT-4 cells were smeared onto slide glasses, dried and fixed with acetone. The presence of the HIV antigen-positive MT-4 cells was detected by the indirect immunofluoroescent assay [Y. Hinuma et al., "Proc. Natl. Acad. Sci. USA," 78, 6476–6480, (1981) and Y. Takeuchi et al., "Gann.", 78, 11–15 (1987)]. To this end, the cell smears, that is, the acetone-fixed cell smears were treated at 37° C. for 30 minutes with such serum of AIDS patient at a dilution of 1:10 in phosphate buffered saline, which was employed as the first antibody. After washing subsequently with phosphate buffered saline, the MT-4 cells were treated at 37° C. for 30 minutes with fluorescent isothiocyanate-conjugated rabbit anti-human IgG serum (Cappel Laboratories, Cocharanville, Pa., USA), which was employed as the second antibody. After the cell smears were then washed with phosphate buffered saline and covered with a cover glass, the MT-4 cells were examined under a fluorescence microscope. Percentages of the number of the viral antigen-positive MT-4 cells (namely, immunofluorescent cells where the HIV-associated antigens were present and expressed) in total cells were calculated.

For the control tests of estimating the number of the total cells under test, the above test procedures were repeated without addition of D-β-lysylmethanediamine.

Furthermore, cytotoxicity of D-β-lysylmethanediamine to the MT-4 cells was estimated. This was done by incubating the MT-4 cells at varying concentrations of D-β-lysylmethanediamine added and in the absence of HIV but in the same manner of incubation and under the same conditions of incubation of MT-4 cells as those employed in the above-mentioned test procedures of assaying the activity of D-β-lysylmethanediamine to inhibit the infection of T-cells with HIV. That the cytotoxicity was not observed is represented by the symbol "-" in Table 1 below.

In order to evaluate the activity of D-β-lysylmethanediamine to inhibit the infection of human T-cells, namely the MT-4 cells with HIV, calculation was made of the percentages (T/C, %) of the number (T) of the HIV antigen-positive cells as measured in the above-mentioned tests where the incubation of MT-4 cells was effected in the presence of the test compound, against the number (C) of the HIV antigen-positive cells as measured in the above-mentioned control tests where the incubation of MT-4 cells was effected without the addition of the test compound. The results of such calculation of the T/C values (%) are shown in Table 1 in term of rate (%) of presence or occurrence of the HIV antigen-positive cells.

TABLE 1

| Concentration of test compound (µg/ml) | Rate (%) of presence of HIV antigen-positive cells | Cytotoxicity |
|---|---|---|
| 3 | 30 | — |
| 10 | 15 | — |
| 30 | 10 | — |
| 100 | 5 | — |

As will be clear from the test results of Table 1 above, it is confirmed that D-β-lysylmethanediamine used in accordance with this invention has no cytotoxicity even at a concentration of 100 µg/ml and can reduce significantly the number of the HIV antigen-positive cells at concentrations of no more than 100 µg/ml, that is to say, can remarkably inhibit the presence of the HIV's viral antigens. 50% Effective concentration ($ED_{50}$) of D-β-lysylmethanediamine against HIV was 0.62 µg/ml.

This fact shows that HIV will not be able to proliferate in the MT-4 cells owing to the presence of D-β-lysylmethanediamine so that the development of the HIV's viral antigens can be inhibited in the human T-cells.

While, it has now been found through recent experiments that D-β-lysylmethanediamine at a concentration of 100 µg/ml shows neither any activity inhibitory to reverse transcriptase of HIV, nor any activity inhibitory to protease of HIV. Thus, it is apparent that D-β-lysylmethanediamine can inhibit strongly the infection of human T-cells with HIV by any mechanism yet unknown.

Incidentally, the above-mentioned tests were repeated concurrently using DDI (namely, 2',3'-dideoxyinosine) which has recently be utilized as a medical drug for treatment of AIDS, and then it has been found that $ED_{50}$ value of DDI against HIV was 0.46 µg/ml, indicating that DDI shows the effect of inhibiting the infection of human T-cells with HIV to the same extent as that of D-β-lysylmethanediamine according to this invention.

In general, D-β-lysylmethanediamine can be administered either orally or parenterally for its actual administration as an antiviral agent for inhibiting the infection with HIV or as an agent for inactivation of HIV according to this invention.

The active ingredient compound used according to this invention, namely D-β-lysylmethanediamine or a salt or hydrate thereof can be administered alone, or it can be administered in the form of a formulation such as an injection, oral preparation, suppository or the like containing the active compound as mixed with an excipient or carrier. Any pharmaceutically acceptable excipients or carriers are selectable for that purpose. The nature and composition of the carrier used may vary depending on the administration route and manner. For example, water, ethanol, an animal or vegetable oil such as soybean oil, sesame oil or mineral oil, or a synthetic oil may be used as a liquid carrier. Usable solid carriers include, for example, a sugar such as maltose or sucrose, an amino acid such as lysine, a cellulose derivative such as hydroxypropylcellulose, a polysaccharide such as cyclodextrin, a salt of an organic acid such as magnesium stearate, or the like.

In the case of the injections being prepared, it is generally preferable that the liquid medium of the injections comprises physiological saline, various buffered solutions, an aqueous solution of a sugar such as glucose, inositol or mannitol, or a glycol such as ethylene glycol or polyethylene glycol. It is also feasible to formulate a lyophilized preparation containing D-β-lysylmethanediamine, a salt or hydrate thereof as the active ingredient associated with an excipient, e.g., a sugar such as inositol, mannitol, glucose, mannose, maltose or sucrose or an amino acid such as phenylalanine. Upon administration, such lyophilized preparation may be dissolved in a suitable solvent for injection, for example, sterilized water or an intravenously-administrable liquid such as physiological saline, aqueous solution of glucose, an aqueous solution of electrolytes or an aqueous solution of amino acids.

Although the proportion of D-β-lysylmethanediamine present in the formulated composition may widely vary from one preparation to another preparations, it may generally be in a range of 0.1–100% by weight, preferably 1–90% by weight. In the case of the preparation of an injection, for example, it is generally desirable that the injectionable solution contains D-β-lysylmethanediamine as active ingredient at a concentration of 0.1–5% by weight. For oral administration, the compound as active ingredient may be formulated into tablets, capsules, a powder, granules in combination with the solid carrier or may be formulated into a solution, a dry syrup or the like in combination with the liquid carrier. In capsules, tablets, granules or a powder, the proportion of D-β-lysylmethanediamine as the active ingredient present therein may generally be in a range of about 3–100 wt. %, preferably 5–90 wt. %, with the balance being formed of a carrier.

The dosage of D-β-lysylmethanediamine may suitably be determined in account of the age, body weight, symptom of patients and therapeutic purpose as intended. The therapeutic, i.e., effective dosage of D-β-lysylmethanediamine may be generally in a range of 1–100 mg/kg/day for the parenteral administration and in a range of 5–500 mg/kg/day for the oral administration. This dosage can be administered either continuously or intermittently as long as the total dosage does not exceed such a specific level that was decided in view of results of animal tests and various circumstances.

Similarly, the total dosage given by the parenteral administration may, of course, vary suitably depending on the way of administration, conditions of the patient or animal under treatment, for example, the age, body weight, sex, sensitivity, foods or feed, administration time, administration route, drugs administered concurrently, conditions of the patient and disease. The suitable dosage and administration frequency of D-β-lysylemthanediamine under given conditions must be determined by an expert physician through the tests of determining optimal dosage and in light of the above guidelines. These requirements for administration should also apply to the oral administration of D-β-lysylmethanediamine.

This invention is now illustrated with reference to the following Examples which show various forms of the compositions for inhibiting the infection with HIV according to this invention.

FORMULATION EXAMPLE 1

An amount of purified water was added to 10 g of D-β-lysylmethanediamine hydrochloride. After dissolution of the hydrochloride compound in water, the solution (100 ml) thus prepared was subjected to sterilizing filtration by passing through a microporous filter of a tradename "Millipore Filter GS". One mililiter of the sterile filtrate so obtained were taken into each 5 ml-vial and then lyophilized to obtain a lyophilized preparation for injection which contained 100 mg of D-β-lysylmethanediamine hydrochloride per vial.

FORMULATION EXAMPLE 2

5 g of D-β-lysylmethanediamine hydrochloride, 60 g of lactose, 33 g of crystalline cellulose and 2 g of hydroxypropylcellulose were mixed together thoroughly. The resultant powdery mixture was pressed by a roll-type pressing machine (Roller Compactor, trade mark) and then the resulting compressed solids were crushed. The thus-crushed material was sifted. The fraction of the resulting granules which were of sizes between 16 mesh and 60 mesh was collected as the desired granular preparation.

FORMULATION EXAMPLE 3

3 g of D-β-lysylmethanediamine, 12 g of crystalline lactose, 5 g of crystalline cellulose and 0.3 g of magnesium stearate were mixed together in a V-model mixer and compressed into tablets each containing 50 mg of D-β-lysylmethanediamine as the active ingredient per tablet.

The production of D-β-lysylemthanediamine may be carried out by inoculating *Streptomyces nashvillensis* MD743-GF4. strain to a culture medium containing such nutrient sources which can be utilized by ordinary microorganisms, and then cultivating said strain, preferably under aerobic conditions. D-β-lysylmethanediamine is thus produced and accumulated primarily in the culture broth and may be recovered from the resulting culture, especially from the culture broth or its filtrate.

The nutrient sources available in the culture medium to be used for the cultivation of said strain may be any of the conventional carbon and nitrogen sources which have been useful as nutrient sources for the cultivation of known strains of Actinomycetes. For example, the assimilable nitrogen sources may include soybean meal, peanut meal, cotton seed meal, dried yeast, peptone, meat extract, casein, corn steep liquor, sodium nitrate and ammonium sulfate which are commercially available. The assimilable carbon sources may include carbohydrates such as glucose, galactose, starch, glycerin, maltose dextrin, sucrose, lactose or soybean oil and fats which are commercially available. The culture medium may also contain inorganic salts such as sodium chloride, calcium carbonate, magnesium sulfate, manganese chloride, ammonium sulfate and phosphates, as well as various amino acids. All the nutrient materials available for the cultivation of known actinomycetes may be used for the cultivation of said MD743-GF4 strain, if they are utilizable by the D-β-lysylmethanediamine-producing strain and are useful for this microorganism to produce D-β-lysylmethanediamine.

In the cultivation of said MD743-GF4 strain, submerged liquid cultivation method under aeration and agitation is preferred for the production of D-β-lysylmethanediamine in a commercial scale. The cultivation temperature may be chosen within the range of temperatures at which the D-β-lysylmethanediamine-producing strain can grow and can produce the desired D-β-lysylmethanediamine. Especially, the cultivation temperature may preferably be at 25° to 30° C. The cultivation of the MD743-GF4 strain may usually be continued until D-β-lysylmethanediamine is produced and accumulated in a sufficient amount in the resulting culture. Normally, the cultivation may be effected for 2 to 7 days.

D-β-Lysylmethanediamine, its acid addition salts and hydrate are well soluble in water and may primarily be present in the liquid portion of the culture broth of the D-β-lysylmethanediamine-producing strain. D-β-Lysylmethanediamine which is present in the liquid portion of the culture substantially connot be extracted with butanol, butyl acetate, chloroform and other organic solvents, and thus the treatments of the broth filtrate with these organic solvents are utilizable, if necessary, in order to remove from the culture broth the undesired compounds or impurities which are present therein. D-β-Lysylmethanediamine present in the culture broth or in aqueous solutions may be recovered by adsorption using various kinds of adsorbents. When active carbon is used as the adsorbent, D-β-lysylmethanediamine as adsorbed can be desorbed from active carbon by eluting with weakly acidic water, or weakly acidic aqueous methanol, aqueous propanol, aqueous acetone and the like.

As D-β-lysylmethanediamine is of the basic nature, this compound is efficiently adsorbable by a cation-exchange resin and is elutable from the resin with suitable eluents. The cation-exchangers available for this purpose include cation-exchange resins containing carboxylic functions in the H-form, Na-form or $NH_4$-form, such as Amberlite IRC-50, Amberlite CG-50 (tradenames, product of Rohm & Haas Co., U.S.A.), Lewatit CNP (tradename, a product of Bayer Co., Germany) and CM-Sephadex (tradename, products of Pharmacia Co., Sweden), either alone or in mixture. The antibiotic as adsorbed by the resin may efficiently be eluted from the resin using acidic water, diluted aqueous ammonia or aqueous solutions of inorganic salts and the like. The elution may usually be made using 0.2 N–1 N hydrochloric acid and 0.5 N–2 N aqueous ammonia. D-β-Lysylmethanediamine is substantially not adsorbable by an anion-exchange resin and this can be utilized for neutralization of acidic solutions containing said compound or for removal of acidic impurities from said compound.

D-β-Lysylmethanediamine may be obtained in its purified form by conducting the above-mentioned extraction methods and separation methods in proper combination or repeating one or more of these methods.

Microbiological properties of the D-β-lysylmethanediamine-producing strain, Streptomyces nashvillensis MD743-GF4 strain, are described in the specification of the aforesaid Japanese patent application first publication "Kokai" Sho-62-114947 in details. A summary of microbiological properties of this MD743-GF4 strain is given below.

Under microscope, it is observed that the MD743-GF4 strain has branched substrate mycelia from which aerial hyphae develop in the form of spirals. No whirls is formed. The chains of mature spores have a chain of more than 20 spores, and spores are measuring 0.6–0.7×1.4–1.7 microns in size and have smooth surfaces. On various culture media, the MD743-GF4 strain shows that the growth of colorless to faintly yellowish brown or lightly brown color is formed with development of aerial hyphae of White to brightly brownish gray color and that soluble pigment is not formed in almost cases, or soluble pigment of yellowish color is slightly formed. The formation of the melanoid pigment is positive. The grade of the protein-decomposing activity of the MD743-GF4 strain is medium but the grade of the starch-hydrolyzing activity is rather strong.

On comparison, the MD743-GF4 strain is well coincident with a known microorganism, Streptomyces nashvillensis IMC S-0342 (ISP 5314) (see the "International Journal of Systematic Bacteriology" Vol. 19, page 455 (1969)) except that the MD743-GF4 strain does not show utilization of D-xylose while the IMC S-0342 strain (ISP 5314) shows utilization of D-xylose.

Streptomyces nashvillensis MD743-GF4 strain mentioned above was deposited on 7 Sep. 1985 (as FERM P-8442) and again deposited on 25 Dec. 1991 and has been deposited in an authorized Japanese depository "Fermentation Research Institute", Agency of Industrial Science and Technology, Ministry of International Trade and Industry, Japan, under the deposit number "FERM P-12676" since 25 Dec. 1991. The MD743-GF4 strain has now been deposited in said "Fermentation Research Institute" under the access number "FERM BP-4127" as transferred in terms of Budapest Treaty. This "Fermentation Research Institute" locates in Tsukuba-city, Ibaragi-ken, Japan.

Next, an example of the fermentative production of D-β-lysylmethanediamine is described in the following Referential Example 1.

Referential Example 1

A quantity of Streptomyces nashvillensis MD743-GF4 strain (FERM P-12676, but now "FERM BP-4127"), which had been incubated in a slant agar medium, was inoculated into a liquid culture medium comprising 2.0% galactose, 2.0% dextrin, 1.0% peptone (available under tradename "Bacto-Soytone", a product of Difco Co.), 0.5% corn steep liqor (a product of Ajinomoto Co.), 0.2% ammonium sulfate and 0.2% calcium carbonate which was placed in 110 ml-portions in conical flasks of 500 ml-capacity. The inoculated culture medium was incubated at 28° C. for 2 days under rotatory shaking (180 rpm.) to provide a first seed culture. This first seed culture was inoculated in 2 ml-portions into 110 ml-portions of the liquid culture medium of the same composition as above, which were placed in 90 conical flasks. The inoculated culture media in these 90 flasks were incubated for 3 days under the same conditions for the incubation as described above.

The culture broths so obtained were collected, combined together and filtered to give 9000 ml of the culture broth filtrate (pH 6.0, with a potency of 80 μg/ml). This filtrate was passed through a column of 550 ml of a cation-exchange resin, Amberlite IRC-50 (a mixture of the $NH_4$-form and H-form, 7:3) to effect adsorption of D-β-lysylmethanediamine by the resin. The resin column was then washed with 1,100 ml of water and subsequently eluted with 1.2N aqueous ammonia. The active fractions of the eluate were collected, combined (1370 ml) and concentrated to dryness under reduced pressure to obtain 636 mg of a crude powder (with a potency of 644 μg/mg).

This crude powder was dissolved in 10 ml of water and the resulting aqueous solution was passed through a column of 60 ml of Amberlite CG-50 ($NH_4$-form) for adsorption of the active compound. This resin column was then washed with 120 ml of water (with the effluent from the column being collected as fractions Nos. 1 to 18), followed by washing with 300 ml of 0.6N aqueous ammonia (with the effluent being collected as fractions Nos. 19 to 60). Finally, the resin column was eluted with 300 ml of 1.2N aqueous ammonia to give fractions Nos. 61 to 101 of the eluate.

The fractions Nos. 77 to 95 were combined together and concentrated to dryness under reduced pressure and further dried to afford D-β-lysylmethanediamine hemicarbonate in the form of a colorless powdery substance which was hygroscopic. The yield was 370 mg (with a potency of 1,000 μg/mg) and the yield based on the culture broth was calculated as 50.8%. This substance showed a specific optical rotation $[\alpha]_D^{26}$ −7.4° (c 0.5, water) When this substance has adsorbed water, it became a colorless syrup.

INDUSTRIAL UTILIZABILITY

As described hereinbefore, it has now been found in accordance with this invention that D-β-lysylmethanediamine, a salt or hydrate thereof has an activity of inhibiting the infection with AIDS virus (virus causative of acquired human immunodeficiency syndrome), namely HIV. A pharmaceutical composition containing the above compound or a salt or hydrate thereof as active ingredient is provided and expectable as one of remedial agents for treating AIDS which is now thought to be difficult to cure.

We claim:

1. A method for inhibiting infection of human T-cells with AIDS virus, which comprises treating human T-cells in vitro with D-β-lysylmethanediamine of the formula (I)

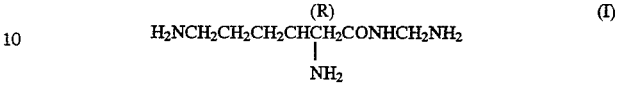

pharmaceutically acceptable salt or hydrate thereof in an effective amount to inhibit the infection with said AIDS virus.

* * * * *